United States Patent
Rao et al.

(10) Patent No.: US 11,098,287 B2
(45) Date of Patent: Aug. 24, 2021

(54) 17β-HYDROXYSTEROID DEHYDROGENASE MUTANTS AND APPLICATION THEREOF

(71) Applicant: Jiangnan University, Wuxi (CN)

(72) Inventors: Zhiming Rao, Wuxi (CN); Minglong Shao, Wuxi (CN); Yetong Wang, Wuxi (CN); Yuling Wu, Wuxi (CN); Taowei Yang, Wuxi (CN); Xian Zhang, Wuxi (CN); Meijuan Xu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/094,982

(22) Filed: Nov. 11, 2020

(65) Prior Publication Data

US 2021/0087539 A1     Mar. 25, 2021

(30) Foreign Application Priority Data

Sep. 10, 2020   (CN) .......................... 202010945382.0

(51) Int. Cl.
| | |
|---|---|
| *C12N 9/04* | (2006.01) |
| *C12N 1/20* | (2006.01) |
| *C12N 15/70* | (2006.01) |
| *C12N 15/52* | (2006.01) |
| *C12P 33/02* | (2006.01) |

(52) U.S. Cl.
CPC ............ *C12N 9/0006* (2013.01); *C12N 1/20* (2013.01); *C12N 15/52* (2013.01); *C12N 15/70* (2013.01); *C12P 33/02* (2013.01); *C12Y 101/01051* (2013.01)

(58) Field of Classification Search
None
See application file for complete search history.

(56) References Cited

U.S. PATENT DOCUMENTS

2021/0087539 A1 *   3/2021   Rao ..................... C12P 33/02

OTHER PUBLICATIONS

Gen Bank Accession No. XP_007688281.1, published May 1, 2014 (Year: 2014).*

* cited by examiner

*Primary Examiner* — Richard C Ekstrom
(74) *Attorney, Agent, or Firm* — IPro, PLLC; Na Xu

(57) ABSTRACT

The disclosure discloses 17β-hydroxysteroid dehydrogenase mutants and application thereof, and belongs to the technical field of biology. The disclosure provides 17β-hydroxysteroid dehydrogenase mutants V107A, T155N, H164Y and V107A/T155N/H164Y with high specific enzyme activities, and the specific enzyme activities of the 17β-hydroxysteroid dehydrogenase mutants V107A, T155N, H164Y and V107A/T155N/H164Y are as high as 1.85, 1.93, 2.06 and 5.15 U/mg, respectively, which are 1.11, 1.16, 1.24 and 3.10 times larger than that of wild-type 17β-hydroxysteroid dehydrogenase (1.66 U/mg).

9 Claims, 1 Drawing Sheet
Specification includes a Sequence Listing.

> # 17β-HYDROXYSTEROID DEHYDROGENASE MUTANTS AND APPLICATION THEREOF

TECHNICAL FIELD

The disclosure relates to 17β-hydroxysteroid dehydrogenase mutants and application thereof, and belongs to the technical field of biology.

BACKGROUND

Steroid drugs have important physiological functions, have an indispensable position in the steroid medicine industry and clinical treatment, and are the most important drugs besides antibiotics. The main steroid drugs produced at this stage are steroid hormone (steroid hormones) drugs.

Boldenone is an important steroid hormone drug, which can be derived from testosterone. Therefore, it has most of the properties of testosterone. For example, boldenone, like testosterone, can be used to promote muscle growth and improve muscle endurance and recovery ability. Moreover, compared with testosterone, boldenone has a lower rate of aromatic hydrocarbons and lower possibility of transformation to estrogen. Therefore, boldenone can be used medically to treat muscle loss and osteoporosis, as well as to increase weight, improve strength and appetite, and retain muscles and tighten muscles for athletes in the off-season.

At present, the chemical method is mostly used to synthesize boldenone. However, the synthesis of boldenone by a chemical method has the disadvantages of low yield, many by-products, complex synthetic route, need for addition of strong acid or toxic reagents, and relatively high cost, etc., which cannot meet the requirements of industrial production. In addition, the process of synthesizing boldenone by the chemical method will produce a large amount of waste gas, waste water and waste materials, which will seriously pollute the environment and do not meet the green requirements of modern industry.

There are also attempts to synthesize boldenone by biological methods. The biological method mainly comprises adding 17β-hydroxysteroid dehydrogenase to estrone and androstenedione with low biological activity to be transformed to produce boldenone with high biological activity. Compared with chemical methods, the biological methods naturally have the advantages of relatively simple process, environmental friendliness and low cost. However, the existing biological method still has big defects. For example, Chen et al. constructed recombinant *Pichia pastoris* by expressing 3-ketosteroid-$\Delta^1$-dehydrogenase using *Pichia pastoris* GS115 as a host. Through the endogenous 17β-hydroxysteroid dehydrogenase of *Pichia pastoris* GS115, the recombinant *Pichia pastoris* can be transformed to produce boldenone by using 4-androstenedione as a substrate (the yield is 41%). However, since the specific enzyme activity of the endogenous 17β-hydroxysteroid dehydrogenase of *Pichia pastoris* GS115 is not high, when the recombinant *Pichia pastoris* is used to produce boldenone, a large amount of 1,4-androstenedione will be produced, and there are many by-products (see references: Chen M M, Wang F Q, Lin L C, et al. Characterization and application of fusidane antibiotic biosynethsis enzyme 3-ketosteroid-1-dehydrogenase in steroid transformation [J]. Applied Microbiology and Biotechnology, 2012, 96(1): 133-142.).

Therefore, there is an urgent need to find a 17β-hydroxysteroid dehydrogenase with high enzymatic activity to overcome the existing defects of synthesis of boldenone by the biological method.

SUMMARY

Technical Problem

The technical problem to be solved by the disclosure is to provide a 17β-hydroxysteroid dehydrogenase with high enzyme activity.

Technical Solutions

In order to solve the above-mentioned problems, the disclosure provides a 17β-hydroxysteroid dehydrogenase mutant. Compared with the 17β-hydroxysteroid dehydrogenase having a starting amino acid sequence shown in SEQ ID NO. 2, the 17β-hydroxysteroid dehydrogenase mutant has a mutation of valine at position 107 to alanine, named V107A.

Alternatively, compared with the 17β-hydroxysteroid dehydrogenase having a starting amino acid sequence shown in SEQ ID NO. 2, the 17β-hydroxysteroid dehydrogenase mutant has a mutation of threonine at position 155 to asparagine, named T155N.

Alternatively, compared with the 17β-hydroxysteroid dehydrogenase having a starting amino acid sequence shown in SEQ ID NO. 2, the 17β-hydroxysteroid dehydrogenase mutant has a mutation of histidine at position 164 to tyrosine, named H164Y.

Alternatively, compared with the 17β-hydroxysteroid dehydrogenase having a starting amino acid sequence shown in SEQ ID NO. 2, the 17β-hydroxysteroid dehydrogenase mutant has a mutation of valine at position 107 to alanine, a mutation of threonine at position 155 to asparagine, and a mutation of histidine at position 164 to tyrosine, named V107A/T155N/H164Y.

In one embodiment of the disclosure, the nucleotide sequence of a gene encoding the 17β-hydroxysteroid dehydrogenase is shown in SEQ ID NO. 1.

The disclosure further provides a gene, which encodes the above-mentioned 17β-hydroxysteroid dehydrogenase mutant.

The disclosure further provides a recombinant plasmid, which carries the above-mentioned gene.

In one embodiment of the disclosure, the expression vector of the recombinant plasmid is pET-28a plasmid.

The disclosure further provides a host cell, wherein the host cell carries the above-mentioned gene or the above-mentioned recombinant plasmid.

In one embodiment of the disclosure, the host cell is *Escherichia coli*.

The disclosure further provides a method for producing boldenone. The method comprises adding the above-mentioned host cell to a transformation system containing 1,4-androstenedione (ADD) to be transformed to obtain a transformation solution containing boldenone; and separating the transformation solution containing boldenone to obtain boldenone.

In one embodiment of the disclosure, the transformation temperature is 35 to 40° C. and the pH is 7.0 to 8.0.

In one embodiment of the disclosure, the transformation temperature is 37° C. and the pH is 7.5.

In one embodiment of the disclosure, the transformation system further contains methylated-β-cyclodextrin.

In one embodiment of the disclosure, in the transformation system, the mass ratio of 1,4-androstenedione to methylated-β-cyclodextrin is 1:3.

The disclosure also provides application of the above-mentioned 17β-hydroxysteroid dehydrogenase mutant or the above-mentioned gene or the above-mentioned recombinant plasmid or the above-mentioned host cell or the above-mentioned method for producing boldenone in the production of boldenone.

The disclosure provides the 17β-hydroxysteroid dehydrogenase mutants V107A, T155N, H164Y and V107A/T155N/H164Y with high specific enzyme activities, and the specific enzyme activities of the 17β-hydroxysteroid dehydrogenase mutants V107A, T155N, H164Y and V107A/T155N/H164Y are as high as 1.85, 1.93, 2.06 and 5.15 U/mg, respectively, which are 1.11, 1.16, 1.24 and 3.10 times larger than that of the wild-type 17β-hydroxysteroid dehydrogenase (1.66 U/mg).

The disclosure provides the engineered $E.\ coli$ BL21/pET28a-HSDBo$^{V107A}$, $E.\ coli$ BL21/pET28a-HSDBo$^{T155N}$, $E.\ coli$ BL21/pET28a-HSDBo$^{H164Y}$ and $E.\ coli$ BL21/pET28a-HSDBo$^{V107A/T155N/H164Y}$, which can produce boldenone at high yield, the engineered $E.\ coli$ BL21/pET28a-HSDBo$^{V107A}$, $E.\ coli$ BL21/pET28a-HSDBo$^{T155N}$, $E.\ coli$ BL21/pET28a-HSDBo$^{H164Y}$ and $E.\ coli$ BL21/pET28a-HSDBo$^{V107A/T155N/H164Y}$ express the genes encoding the 17β-hydroxysteroid dehydrogenase mutants V107A, T155N, H164Y and V107A/T155N/H164Y by using $E.\ coli$ BL21 as the host, and the engineered $E.\ coli$ BL21/pET28a-HSDBo$^{V107A}$, $E.\ coli$ BL21/pET28a-HSDBo$^{T155N}$, $E.\ coli$ BL21/pET28a-HSDBo$^{H164Y}$ and $E.\ coli$ BL21/pET28a-HSDBo$^{V107A/T155N/H164Y}$ are respectively added to the transformation system containing 1,4-androstenedione to be transformed for 24 h, so that the yields of boldenone in the transformation solution are as high as 2.12, 2.20, 2.16, and 2.49 g/L, respectively, which are 1.11, 1.15, 1.18 and 1.30 times larger than that of the engineered $E.\ coli$ BL21/pET28a-HSDBo (1.91 g/L).

DETAILED DESCRIPTION

Figure 1:
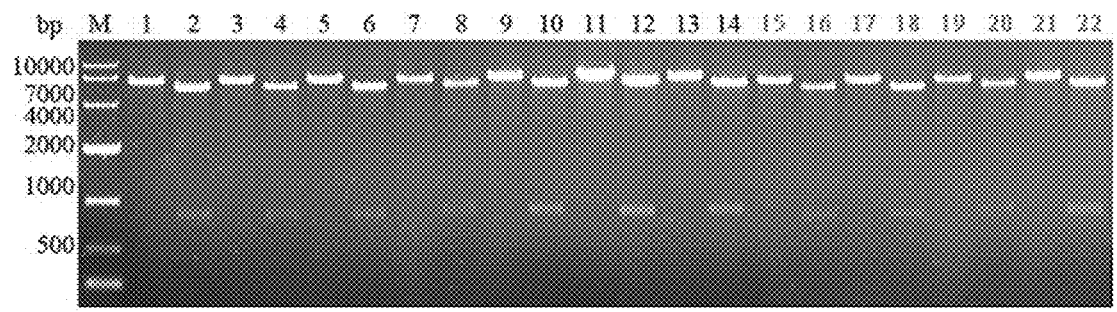
FIG. 1: Enzyme digestion verification results of different recombinant plasmids; in which, M: DNA Marker; 1, 3, 5, 7, 9, 11, 13, 15, 17, 19, 21: recombinant plasmids digested with BamH I: pET28a-HSDBo$^{V106L}$, pET28a-HSDBo$^{V107A}$, pET28a-HSDBo$^{F109D}$, pET28a-HSDBo$^{N154S}$, pET28a-HSDBo$^{T155N}$, pET28a-HSDBo$^{D158R}$, pET28a-HSDBo$^{F159G}$, pET28a-HSDBo$^{V161F}$, pET28a-HSDBo$^{H164Y}$, pET28a-HSDBo$^{V208G}$ and pET28a-HSDBo$^{V107A/T155N/H164Y}$; 2, 4, 6, 8, 10, 12, 14, 16, 18, 20, 22: recombinant plasmids digested with BamH I and Sac I: pET28a-HSDBo$^{V106L}$, pET28a-HSDBo$^{V107A}$, pET28a-HSDBo$^{F109D}$, pET28a-HSDBo$^{N154S}$, pET28a-HSDBo$^{T155N}$, pET28a-HSDBo$^{D158R}$, pET28a-HSDBo$^{F159G}$, pET28a-HSDBo$^{V161F}$, pET28a-HSDBo$^{H164Y}$, pET28a-HSDBo$^{V208G}$, and pET28a-HSDBo$^{V107A/T155N/H164Y}$.

The $Escherichia\ coli$ BL21 involved in the following examples was purchased from Invitrogen company; the pET-28a plasmid involved in the following examples was purchased from Novagen company; 1,4-androstenedione (ADD) and boldenone involved in the following examples were purchased from SIGMA company, USA; Ellman reagent (DTNB) and cysteine involved in the following examples were purchased from Shanghai Aladdin Biochemical Technology Co., Ltd.

The media and reagents involved in the following examples are as follows:

LB liquid medium: peptone 10 g/L, yeast extract 5 g/L, NaCl 10 g/L.

LB solid medium: peptone 10 g/L, yeast extract 5 g/L, NaCl 10 g/L, agar 20 g/L.

The detection methods involved in the following examples are as follows:

Determination of 1,4-androstenedione and boldenone contents: An HPLC method was used to determine the product concentration; in which, the chromatographic conditions are as follows: chromatographic column: DimosoilC18 (5 μL, 250 mm×4.6 mm), mobile phase: methanol-water (V/V=70:30), detector: UV Detector, detection wavelength: 254 nm, column temperature: 30° C., injection volume: 5 μL, and flow rate: 1.0 mL/min.

Determination of enzyme activity of 17β-hydroxysteroid dehydrogenase: The reaction system (2 mL) contains a 10 mM phosphate buffer (pH 7.5), 200 μM 1,4-androstenedione pre-dissolved in 2% (v/v) methanol, 0.5 mM NADPH and an appropriate amount of purified 17β-hydroxysteroid dehydrogenase; after the reaction system reacted in a 37° C. water bath for 1 h, the reaction was terminated after reacting in a boiling water bath for 5 min, a supernatant was taken by centrifuging, and the content of boldenone in the supernatant was determined by the HPLC method, and then the enzyme activity of 17β-hydroxysteroid dehydrogenase was calculated.

The enzymatic activity of 17β-hydroxysteroid dehydrogenase is defined as: the amount of enzyme required to transform 1 µmol 1,4-androstenedione to produce boldenone under the conditions of 37° C. and pH 7.5 is defined as one enzyme activity unit (1 U).

Determination of specific enzyme activity of 17β-hydroxysteroid dehydrogenase: Specific enzyme activity of 17β-hydroxysteroid dehydrogenase=enzyme activity/protein concentration;

The protein concentration was determined by the Bradford method, and the Bradford method was recorded in the reference "Bradford, M M 1976. A rapid and sensitive method for the quantitation of microgram quantities of protein utilizing the principle of protein-dyebinding. Anal. Biochem. 72:248-254."

Example 1: Preparation of 17β-Hydroxysteroid Dehydrogenase Mutants

Specific steps are as follows:

1. Construction of Recombinant E. coli

The pET-28a plasmid was transformed into *Escherichia coli* BL21 to obtain a transformation product; the transformation product was applied to the LB solid medium (containing 50 µg-mL$^{-1}$ kanamycin), and inverted and cultured in a 37° C. constant temperature incubator for 8 to 12 h to obtain transformants; the transformants were picked, the LB liquid medium was inoculated with the transformants, the transformants were cultured in a shake flask at 37° C. and 180 rpm for 8 to 12 h, and then the plasmid was extracted for enzyme digestion verification and sequencing verification, and the engineered *E. coli* BL21/pET28a was obtained if the verification was correct.

The gene encoding 17β-hydroxysteroid dehydrogenase (SEQ ID NO. 2) having a nucleotide sequence shown in SEQ ID NO. 1 was synthesized; the gene encoding 17β-hydroxysteroid dehydrogenase was used as a template and HSDBo-F and HSDBo-R were used as primers (see Table 1 for details) to perform PCR amplification to obtain an amplified product; the amplified product was ligated to the pET-28a plasmid digested with restriction enzymes BamH I and Hind III to obtain a ligation product; the ligation product was transformed into *E. coli* BL21 to obtain a transformation product; the transformation product was applied to the LB solid medium (containing 50 µg-mL$^{-1}$ kanamycin), and inverted and cultured in a 37° C. constant temperature incubator for 8 to 12 h to obtain transformants; the transformants were picked, the LB liquid medium was inoculated with the transformants, the transformants were cultured in a shake flask at 37° C. and 180 rpm for 8 to 12 h, and then the plasmid was extracted for enzyme digestion verification and sequencing verification, and the recombinant plasmid pET28a-HSDBo and the engineered *E. coli* BL21/pET28a-HSDBo were obtained if the verification was correct.

Using fusion PCR technology, the recombinant plasmid pET28a-HSDBo was used as a template, and HSDBo$^{V106L}$-F and HSDBo$^{V106L}$-R, HSDBo$^{V107A}$-F and HSDBo$^{V107A}$-R, HSDBo$^{F109D}$-F and HSDBo$^{F109D}$-R, HSDBo$^{N154S}$-F and HSDBo$^{N154S}$-R, HSDBo$^{T155N}$-F and HSDBo$^{T155N}$-R, HSDBo$^{D158R}$-F and HSDBo$^{D158R}$-R, HSDBo$^{F159G}$-F and HSDBo$^{F159G}$-R, HSDBo$^{V161F}$-F and HSDBo$^{V161F}$-R, HSDBo$^{H164Y}$-F and HSDBo$^{H164Y}$-R, HSDBo$^{V208G}$-F and HSDBo$^{V208G}$-R were respectively used as primers (see Table 1 for details) to carry out site-directed mutagenesis to obtain PCR products; the PCR products were transformed into *E. coli* BL21 to obtain transformation products; the transformation products were applied to the LB solid medium (containing 50 µg-mL$^{-1}$ kanamycin), and inverted and cultured in a 37° C. constant temperature incubator for 8 to 12 h to obtain transformants; the transformants were picked, the LB liquid medium was inoculated with the transformants, the transformants were cultured in a shake flask at 37° C. and 180 rpm for 8 to 12 h, then the plasmids were extracted for enzyme digestion verification (see FIG. 1 for the verification results) and sequencing verification (sequencing was completed by Shanghai Sangon), and the recombinant plasmids pET28a-HSDBo$^{V106L}$, pET28a-HSDBo$^{V107A}$, pET28a-HSDBo$^{F109D}$, pET28a-HSDBo$^{N154S}$, pET28a-HSDBo$^{T155N}$, pET28a-HSDBo$^{D158R}$, pET28a-HSDBo$^{F159G}$, pET28a-HSDBo$^{V161F}$, pET28a-HSDBo$^{H164Y}$, pET28a-HSDBo$^{V208G}$ and pET28a-HSDBo$^{V107A/T155N/H164Y}$, and, the engineered *E. coli* BL21/pET28a-HSDBo$^{V106L}$, *E. coli* BL21/pET28a-HSDBo$^{V107A}$, *E. coli* BL21/pET28a-HSDBo$^{F109D}$, *E. coli* BL21/pET28a-HSDBo$^{N154S}$, *E. coli* BL21/pET28a-HSDBo$^{T155N}$, *E. coli* HBL21/pET28a-HSDBo$^{D158R}$, *E. coli* BL21/pET28a-HSDBo$^{F159G}$, *E. coli* BL21/pET28a-HSDBo$^{V161F}$, *E. coli* BL21/pET28a-HSDBo$^{H164Y}$, *E. coli* BL21/pET28a-HSDBo$^{V208G}$ and *E. coli* BL21/pET28a-HSDBo$^{V107A/T155N/H164Y}$ where obtained if the verification was correct.

TABLE 1

Primers used by PCR and nucleotide sequences thereof

| Primers | Sequences (5'-3') |
| --- | --- |
| HSDBo-F | CGGGATCCCGATGCCACACGTAGAAAGCACACCCTCC (SEQ ID NO. 3) |
| HSDBo-R | CGAGCTCGCTATGCGGCACCACCATCCAGCGTAAG (SEQ ID NO. 4) |
| HSDBo$^{V106L}$-F | GCAACTCGGGCCTCGTAAGCTTCGG (SEQ ID NO. 5) |
| HSDBo$^{V106L}$-R | CCGAAGCTTACGAGGCCCGAGTTGC (SEQ ID NO. 6) |
| HSDBo$^{V107A}$-F | ACTCGGGCGTCGCCAGCTTCGGCCA (SEQ ID NO. 7) |
| HSDBo$^{V107A}$-R | TGGCCGAAGCTGGCGACGCCCGAGT (SEQ ID NO. 8) |
| HSDBo$^{F109D}$-F | GCGTCGTAAGCGACGGCCACTTGAA (SEQ ID NO. 9) |
| HSDBo$^{F109D}$-R | TTCAAGTGGCCGTCGCTTACGACGC (SEQ ID NO. 10) |
| HSDBo$^{N154S}$-F | TGACTTCCTCCAGCACCTCGCGCGA (SEQ ID NO. 11) |
| HSDBo$^{N154S}$-R | TCGCGCGAGGTGCTGGAGGAAGTCA (SEQ ID NO. 12) |

TABLE 1-continued

Primers used by PCR and nucleotide sequences thereof

| Primers | Sequences (5'-3') |
|---|---|
| HSDBo$^{T155N}$-F | CTTCCTCCAACAACTCGCGCGACTT (SEQ ID NO. 13) |
| HSDBo$^{T155N}$-R | AAGTCGCGCGAGTTGTTGGAGGAAG (SEQ ID NO. 14) |
| HSDBo$^{D158R}$-F | ACACCTCGCGCAGGTTTAGCGTGCC (SEQ ID NO. 15) |
| HSDBo$^{D158R}$-R | GGCACGCTAAACCTGCGCGAGGTGT (SEQ ID NO. 16) |
| HSDBo$^{F159G}$-F | CCTCGCGCGACGGTAGCGTGCCAAA (SEQ ID NO. 17) |
| HSDBo$^{F159G}$-R | TTTGGCACGCTACCGTCGCGCGAGG (SEQ ID NO. 18) |
| HSDBo$^{V161F}$-F | GCGACTTTAGCTTCCCAAAGCACTC (SEQ ID NO. 19) |
| HSDBo$^{V161F}$-R | GAGTGCTTTGGGAAGCTAAAGTCGC (SEQ ID NO. 20) |
| HSDBo$^{H164Y}$-F | GCGTGCCAAAGTACTCGCTGTACTC (SEQ ID NO. 21) |
| HSDBo$^{H164Y}$-R | GAGTACAGCGAGTACTTTGGCACGC (SEQ ID NO. 22) |
| HSDBo$^{V208G}$-F | TGTTTCATGAGGGTTCGCATCATTA (SEQ ID NO. 23) |
| HSDBo$^{V208G}$-R | TAATGATGCGAACCCTCATGAAACA (SEQ ID NO. 24) |

2. Preparation of 17β-Hydroxysteroid Dehydrogenase Mutants

Figure 2:
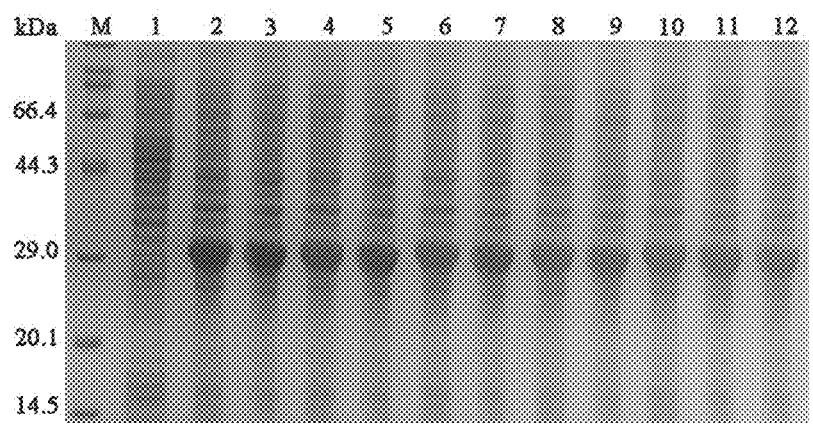
FIG. 2: SDS-PAGE analysis results of cell disruption supernatants obtained by fermentation of different recombinant $E.\ coli$; in which, M: protein Marker; 1: cell disruption supernatant obtained by fermentation of $E.\ coli$ BL21/pET28a; 2: cell disruption supernatant obtained by fermentation of $E.\ coli$ BL21/pET28a-HSDBo$^{V106L}$; 3: cell disruption supernatant obtained by fermentation of $E.\ coli$ BL21/pET28a-HSDBo$^{V107A}$; 4: cell disruption supernatant obtained by fermentation of $E.\ coli$ BL21/pET28a-HSDBo$^{F109D}$; 5: cell disruption supernatant obtained by fermentation of $E.\ coli$ BL21/pET28a-HSDBo$^{N154S}$; 6: cell disruption supernatant obtained by fermentation of $E.\ coli$ BL21/pET28a-HSDBo$^{T155N}$; 7: cell disruption supernatant obtained by fermentation of $E.\ coli$ BL21/pET28a-HSDBo$^{D158R}$; 8: cell disruption supernatant obtained by fermentation of $E.\ coli$ BL21/pET28a-HSDBo$^{F159G}$; 9: cell disruption supernatant obtained by fermentation of $E.\ coli$ BL21/pET28a-HSDBo$^{V161F}$; 10: cell disruption supernatant obtained by fermentation of $E.\ coli$ BL21/pET28a-HSDBo$^{H164Y}$; 11: cell disruption supernatant obtained by fermentation of $E.\ coli$ BL21/pET28a-HSDBo$^{V208G}$; 12: cell disruption supernatant obtained by fermentation of $E.\ coli$ BL21/pET28a-HSDBo$^{V107A/T155N/H164Y}$.
Figure 3:
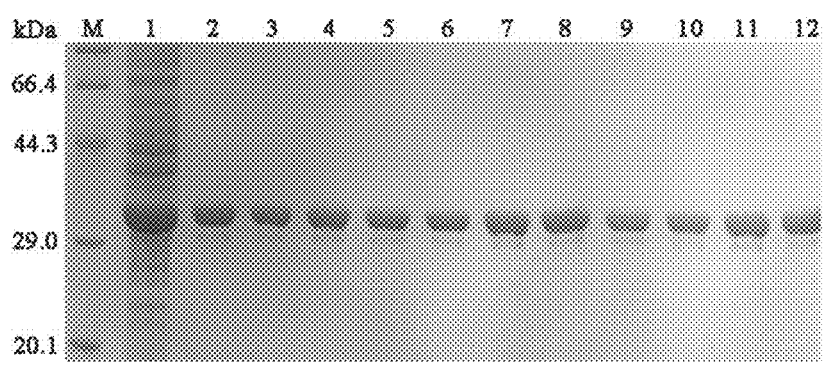
FIG. 3: SDS-PAGE analysis results of different purified 17β-hydroxysteroid dehydrogenase mutants; in which, M: protein Marker; 1: cell disruption supernatant obtained by fermentation of $E.\ coli$ BL21/pET28a-HSDBo$^{V107A/T155N/H164Y}$; 2: purified 17β-hydroxysteroid dehydrogenase mutant V106L; 3: purified 17β-hydroxysteroid dehydrogenase mutant V107A; 4: purified 17β-hydroxysteroid dehydrogenase mutant F109D; 5: purified 17β-hydroxysteroid dehydrogenase mutant N154S; 6: purified 17β-hydroxysteroid dehydrogenase mutant T155N; 7: purified 17β-hydroxysteroid dehydrogenase mutant D158R; 8: purified 17β-hydroxysteroid dehydrogenase mutant F159G; 9: purified 17β-hydroxysteroid dehydrogenase mutant V161F; 10: purified 17β-hydroxysteroid dehydrogenase mutant H164Y; 11: purified 17β-hydroxysteroid dehydrogenase mutant V208G; 12: purified 17β-hydroxysteroid dehydrogenase mutant V107A/T155N/H164Y.

The engineered E. coli BL21/pET28a, E. coli BL21/pET28a-HSDBo, E. coli BL21/pET28a-HSDBo$^{V106L}$, E. coli BL21/pET28a-HSDBo$^{V107A}$, E. coli BL21/pET28a-HSDBo$^{F109D}$, E. coli BL21/pET28a-HSDBo$^{N154S}$, E. coli BL21/pET28a-HSDBo$^{T155N}$, E. coli BL21/pET28a-HSDBo$^{D158R}$, E. coli BL21/pET28a-HSDBo$^{F159G}$, E. coli BL21/pET28a-HSDBo$^{V161F}$, E. coli BL21/pET28a-HSDBo$^{H164Y}$, E. coli BL21/pET28a-HSDBo$^{V208G}$ and E. coli BL21/pET28a-HSDBo$^{V107A/T155N/H164Y}$ were respectively streaked on the LB solid medium and cultured at 37° C. for 8 to 12 h to obtain single colonies; the single colonies were picked, the LB liquid medium was inoculated with the single colonies, and the single colonies were cultured at 37° C. for 8 to 12 h to obtain a seed liquid; the LB liquid medium was inoculated with the seed liquid at an inoculum amount of 1% (v/v), and the seed liquid was cultured at 37° C. and 180 rpm for 12 to 24 h to obtain a fermentation broth; the fermentation broth was centrifuged to take cells; the cells were disrupted with ultrasonics and centrifuged to obtain cell disruption supernatants (SDS-PAGE analysis results of the cell disruption supernatant are shown in FIG. 2); the cell disruption supernatants were subjected to affinity chromatography on a nickel column to obtain purified wild-type 17β-hydroxysteroid dehydrogenase and 17β-hydroxysteroid dehydrogenase mutants V106L, V107A, F109D, N154S, T155N, D158R, F159G, V161F, H164Y, V208G and V107A/T155N/H164Y (SDS-PAGE analysis results of pure enzymes are shown in FIG. 3).

The specific enzyme activities of the purified wild-type 17β-hydroxysteroid dehydrogenase and 17β-hydroxysteroid dehydrogenase mutants V106L, V107A, F109D, N154S, T155N, D158R, F159G, V161F, H164Y, V208G, and V107A/T155N/H164Y were detected. The detection results were as follows: the specific enzyme activity of the purified wild-type 17β-hydroxysteroid dehydrogenase was 1.66 U/mg, and the specific enzyme activities of the purified 17β-hydroxysteroid dehydrogenase mutants V106L, V107A, F109D, N154S, T155N, D158R, F159G, V161F, H164Y, V208G and V107A/T155N/H164Y were 0.27, 1.85, 1.03, 1.26, 1.93, 1.42, 0.74, 0.67, 2.06, 0.38 and 5.15 U/mg, respectively. It can be seen that only the 17β-hydroxysteroid dehydrogenase mutants V107A, T155N, H164Y and V107A/T155N/H164Y have specific enzyme activities higher than that of the wild-type 17β-hydroxysteroid dehydrogenase.

3. Enzymatic Properties of 17β-Hydroxysteroid Dehydrogenase Mutants 3.1. Optimum Temperature The enzyme activities of the purified wild-type 17β-hydroxysteroid dehydrogenase and 17β-hydroxysteroid dehydrogenase mutants V107A, T155N, H164Y, and V107A/T155N/H164Y were determined at 20 to 60° C. (the temperature gradient interval is 5° C., including 37° C.), and other enzyme activities were compared with the highest enzyme activity of 100% to calculate the relative enzyme activities to investigate the optimal operative temperature of the enzyme.

The detection results are as follows: the optimal temperatures of the wild-type 17β-hydroxysteroid dehydrogenase and 17β-hydroxysteroid dehydrogenase mutants V107A, T155N, H164Y, and V107A/T155N/H164Y are 37° C.

3.2. Optimal pH

After the 10 mM phosphate buffer (pH 7.5) in the reaction system was respectively replaced with a 10 mM Na$_2$HPO$_4$-citrate buffer with pH 4 to 6, a 10 mM Na$_2$HPO$_4$—NaH$_2$PO$_4$ buffer with pH 6 to 8; and a 10 mM Na$_2$CO$_3$—NaHCO$_3$ buffer with pH 8 to 10 (the pH gradient interval is 1, including pH 7.5), the enzyme activities of the purified wild-type 17β-hydroxysteroid dehydrogenase and 17β-hydroxysteroid dehydrogenase mutants V107A, T155N, H164Y, and V107A/T155N/H164Y were determined, and other enzyme activities were compared with the highest enzyme activity of 100% to calculate the relative enzyme activities to investigate the optimal operative pH of the enzyme.

The detection results are as follows: the optimal pH of the wild-type 17β-hydroxysteroid dehydrogenase and 17β-hydroxysteroid dehydrogenase mutants V107A, T155N, H164Y, and V107A/T155N/H164Y is 7.5.

Example 2: Production of Boldenone

Specific steps are as follows:

Taking the engineered *E. coli* BL21/pET28a-HSDBo obtained in Example 1 as a control, the engineered *E. coli* BL21/pET28a-HSDBo$^{V107A}$, *E. coli* BL21/pET28a-HSDBo$^{T155N}$, *E. coli* BL21/pET28a-HSDBo$^{H164Y}$ and *E. coli* BL21/pET28a-HSDBo$^{V107A/T155N/H164Y}$ cells obtained in Example 1 were respectively added at the addition amount of 200 g/L to the transformation system containing a 1 g/L substrate, 1,4-androstenedione, and 3 g/L methyl-ated-β-cyclodextrin (substrate cosolvent) to be transformed at 37° C. and pH 7.5 for 24 h to obtain a transformation solution.

The yield of boldenone in the transformation solution was detected, and the detection results are as follows: the engineered *E. coli* BL21/pET28a-HSDBo$^{V107A}$, *E. coli* BL21/pET28a-HSDBo$^{T155N}$, *E. coli* BL21/pET28a-HSDBo$^{H164Y}$ and *E. coli* BL21/pET28a-HSDBo$^{V107A/T155N/H164Y}$ were respectively added to the transformation system containing 1,4-androstenedione to be transformed for 24 h, so that the yields of boldenone in the transformation solution was as high as 2.12, 2.20, 2.16 and 2.49 g/L, respectively, which were 1.11, 1.15, 1.18, and 1.30 times larger than that of the engineered *E. coli* BL21/pET28a-HSDBo (1.91 g/L).

What is claimed is:

1. A 17β-hydroxysteroid dehydrogenase mutant, wherein the 17β-hydroxysteroid dehydrogenase mutant comprises an amino acid sequence having all of SEQ ID NO: 2 except for:
   a mutation of valine at position 107 to alanine;
   a mutation of threonine at position 155 to asparagine;
   a mutation of histidine at position 164 to tyrosine; or
   a mutation of threonine at position 155 to asparagine, and a mutation of histidine at position 164 to tyrosine.

2. A gene, wherein the gene encodes the 17β-hydroxysteroid dehydrogenase mutant according to claim 1.

3. A recombinant plasmid, wherein the recombinant plasmid carries the gene according to claim 2.

4. A host cell, wherein the host cell carries the gene according to claim 2.

5. The host cell according to claim 4, wherein the host cell is *Escherichia coli*.

6. A method for producing boldenone, comprising: adding the host cell according to claim 4 to a transformation system containing 1,4-androstenedione to be transformed to obtain a transformation solution containing boldenone; and separating the transformation solution containing boldenone to obtain boldenone.

7. The method for producing boldenone according to claim 6, wherein the transformation temperature is 35 to 40° C. and the pH is 7.0 to 8.0.

8. The method for producing boldenone according to claim 6, wherein the transformation system further contains methylated-β-cyclodextrin.

9. A host cell, wherein the host cell comprises the recombinant plasmid according to claim 3.

\* \* \* \* \*

SEQUENCE LISTING

```
<160> NUMBER OF SEQ ID NOS: 24

<210> SEQ ID NO 1
<211> LENGTH: 813
<212> TYPE: DNA
<213> ORGANISM: Artificial sequence
<220> FEATURE:
<223> OTHER INFORMATION: Synthetic DNA

<400> SEQUENCE: 1
atgccacacg tagaaagcac accctccacc tacatccccg ccgcctcga cggcaaagtc      60 gccctcgtca ccggctccgg ccgcggtatc ggcgcagccg tagccacgca cttgggccgt     120
ctaggcgcca aagtcgtcgt caactatgcc aactcgacca agacgccga gaaagtagtc      180 tcagagatca aagcgctcgg cagcgatgcc atcgccatca agccgacat ccgccaagtc      240 ccagacattg tgcgcctctt cgacgaagcc gtcgcgcact cggccacct tgatattgct      300 gttagcaact cgggcgtcgt aagcttcggc cacttgaaag atgtcacaga agaagaattc      360
gaccgcgtct tcagcctcaa cacgcgcggc caattcttcg tcgcccgcga ggcatatcgc      420
cacctgaccg agggcggccg catcatcctg acttcctcca cacctcgcg cgactttagc      480 gtgccaaagc actcgctgta ctctgggtcc aagggcgctg tcgactcgtt cgtccgcatc      540
ttctccaagg actgtggcga taagaagatt acggttaatg cggttgcgcc cggaggaacg     600
gtgacggata tgtttcatga ggtttcgcat cattatattc cgaatgggtt ggactatacg     660
gcggagcagc gtcagcagat ggccgcgcat gcgtcgccgc tgcataggaa tgggttcccg     720
caggatgtgg cgaatgtggt tggtttccta gtaagcaagg agggcgagtg ggtgaatggt     780
aaggttctta cgctggatgg tggtgccgca tag                                  813

<210> SEQ ID NO 2
<211> LENGTH: 270
<212> TYPE: PRT
<213> ORGANISM: Artificial sequence
<220> FEATURE:
<223> OTHER INFORMATION: Protein translated from synthetic DNA

<400> SEQUENCE: 2

Met Pro His Val Glu Ser Thr Pro Ser Thr Tyr Ile Pro Gly Arg Leu
1               5                   10                  15

Asp Gly Lys Val Ala Leu Val Thr Gly Ser Gly Arg Gly Ile Gly Ala
            20                  25                  30

Ala Val Ala Thr His Leu Gly Arg Leu Gly Ala Lys Val Val Val Asn
        35                  40                  45

Tyr Ala Asn Ser Thr Lys Asp Ala Glu Lys Val Val Ser Glu Ile Lys
    50                  55                  60
```

Ala Leu Gly Ser Asp Ala Ile Ala Ile Lys Ala Asp Ile Arg Gln Val
65                  70                  75                  80

Pro Asp Ile Val Arg Leu Phe Asp Glu Ala Val Ala His Phe Gly His
                85                  90                  95

Leu Asp Ile Ala Val Ser Asn Ser Gly Val Val Ser Phe Gly His Leu
            100                 105                 110

Lys Asp Val Thr Glu Glu Glu Phe Asp Arg Val Phe Ser Leu Asn Thr
        115                 120                 125

Arg Gly Gln Phe Phe Val Ala Arg Glu Ala Tyr Arg His Leu Thr Glu
    130                 135                 140

Gly Gly Arg Ile Ile Leu Thr Ser Ser Asn Thr Ser Arg Asp Phe Ser
145                 150                 155                 160

Val Pro Lys His Ser Leu Tyr Ser Gly Ser Lys Gly Ala Val Asp Ser
                165                 170                 175

Phe Val Arg Ile Phe Ser Lys Asp Cys Gly Asp Lys Lys Ile Thr Val
            180                 185                 190

Asn Ala Val Ala Pro Gly Gly Thr Val Thr Asp Met Phe His Glu Val
        195                 200                 205

Ser His His Tyr Ile Pro Asn Gly Leu Asp Tyr Thr Ala Glu Gln Arg
    210                 215                 220

Gln Gln Met Ala Ala His Ala Ser Pro Leu His Arg Asn Gly Phe Pro
225                 230                 235                 240

Gln Asp Val Ala Asn Val Val Gly Phe Leu Val Ser Lys Glu Gly Glu
                245                 250                 255

Trp Val Asn Gly Lys Val Leu Thr Leu Asp Gly Gly Ala Ala
            260                 265                 270

<210> SEQ ID NO 3
<211> LENGTH: 37
<212> TYPE: DNA
<213> ORGANISM: Artificial sequence
<220> FEATURE:
<223> OTHER INFORMATION: Synthetic DNA

<400> SEQUENCE: 3
cgggatcccg atgccacacg tagaaagcac accctcc                              37

<210> SEQ ID NO 4
<211> LENGTH: 35
<212> TYPE: DNA
<213> ORGANISM: Artificial sequence
<220> FEATURE:
<223> OTHER INFORMATION: Synthetic DNA

<400> SEQUENCE: 4
cgagctcgct atgcggcacc accatccagc gtaag                                35

<210> SEQ ID NO 5
<211> LENGTH: 25
<212> TYPE: DNA
<213> ORGANISM: Artificial sequence
<220> FEATURE:
<223> OTHER INFORMATION: Artificial sequence

<400> SEQUENCE: 5
gcaactcggg cctcgtaagc ttcgg                                           25

<210> SEQ ID NO 6
<211> LENGTH: 25

<212> TYPE: DNA
<213> ORGANISM: Artificial sequence
<220> FEATURE:
<223> OTHER INFORMATION: Synthetic DNA

<400> SEQUENCE: 6
ccgaagctta cgaggcccga gttgc                                              25

<210> SEQ ID NO 7
<211> LENGTH: 25
<212> TYPE: DNA
<213> ORGANISM: Artificial sequence
<220> FEATURE:
<223> OTHER INFORMATION: Synthetic DNA

<400> SEQUENCE: 7
actcgggcgt cgccagcttc ggcca                                              25

<210> SEQ ID NO 8
<211> LENGTH: 25
<212> TYPE: DNA
<213> ORGANISM: Artificial sequence
<220> FEATURE:
<223> OTHER INFORMATION: Synthetic DNA

<400> SEQUENCE: 8
tggccgaagc tggcgacgcc cgagt                                              25

<210> SEQ ID NO 9
<211> LENGTH: 25
<212> TYPE: DNA
<213> ORGANISM: Artificial sequence
<220> FEATURE:
<223> OTHER INFORMATION: Synthetic DNA

<400> SEQUENCE: 9
gcgtcgtaag cgacggccac ttgaa                                              25

<210> SEQ ID NO 10
<211> LENGTH: 25
<212> TYPE: DNA
<213> ORGANISM: Artificial sequence
<220> FEATURE:
<223> OTHER INFORMATION: Synthetic DNA

<400> SEQUENCE: 10
ttcaagtggc cgtcgcttac gacgc                                              25

<210> SEQ ID NO 11
<211> LENGTH: 25
<212> TYPE: DNA
<213> ORGANISM: Artificial sequence
<220> FEATURE:
<223> OTHER INFORMATION: Synthetic DNA

<400> SEQUENCE: 11
tgacttcctc cagcacctcg cgcga                                              25

<210> SEQ ID NO 12
<211> LENGTH: 25
<212> TYPE: DNA
<213> ORGANISM: Artificial sequence
<220> FEATURE:
<223> OTHER INFORMATION: Synthetic DNA

<400> SEQUENCE: 12

```
tcgcgcgagg tgctggagga agtca                                             25

<210> SEQ ID NO 13
<211> LENGTH: 25
<212> TYPE: DNA
<213> ORGANISM: Artificial sequence
<220> FEATURE:
<223> OTHER INFORMATION: Synthetic DNA

<400> SEQUENCE: 13
cttcctccaa caactcgcgc gactt                                             25

<210> SEQ ID NO 14
<211> LENGTH: 25
<212> TYPE: DNA
<213> ORGANISM: Artificial sequence
<220> FEATURE:
<223> OTHER INFORMATION: Synthetic DNA

<400> SEQUENCE: 14
aagtcgcgcg agttgttgga ggaag                                             25

<210> SEQ ID NO 15
<211> LENGTH: 25
<212> TYPE: DNA
<213> ORGANISM: Artificial sequence
<220> FEATURE:
<223> OTHER INFORMATION: Synthetic DNA

<400> SEQUENCE: 15
acacctcgcg caggtttagc gtgcc                                             25

<210> SEQ ID NO 16
<211> LENGTH: 25
<212> TYPE: DNA
<213> ORGANISM: Artificial sequence
<220> FEATURE:
<223> OTHER INFORMATION: Synthetic DNA

<400> SEQUENCE: 16
ggcacgctaa acctgcgcga ggtgt                                             25

<210> SEQ ID NO 17
<211> LENGTH: 25
<212> TYPE: DNA
<213> ORGANISM: Artificial sequence
<220> FEATURE:
<223> OTHER INFORMATION: Synthetic DNA

<400> SEQUENCE: 17
cctcgcgcga cggtagcgtg ccaaa                                             25

<210> SEQ ID NO 18
<211> LENGTH: 25
<212> TYPE: DNA
<213> ORGANISM: Artificial sequence
<220> FEATURE:
<223> OTHER INFORMATION: Synthetic DNA

<400> SEQUENCE: 18
tttggcacgc taccgtcgcg cgagg                                             25

<210> SEQ ID NO 19
<211> LENGTH: 25
<212> TYPE: DNA
<213> ORGANISM: Artificial sequence
```

```
<220> FEATURE:
<223> OTHER INFORMATION: Synthetic DNA

<400> SEQUENCE: 19
gcgactttag cttcccaaag cactc                                              25

<210> SEQ ID NO 20
<211> LENGTH: 25
<212> TYPE: DNA
<213> ORGANISM: Artificial sequence
<220> FEATURE:
<223> OTHER INFORMATION: Synthetic DNA

<400> SEQUENCE: 20
gagtgctttg ggaagctaaa gtcgc                                              25

<210> SEQ ID NO 21
<211> LENGTH: 25
<212> TYPE: DNA
<213> ORGANISM: Artificial sequence
<220> FEATURE:
<223> OTHER INFORMATION: Synthetic DNA

<400> SEQUENCE: 21
gcgtgccaaa gtactcgctg tactc                                              25

<210> SEQ ID NO 22
<211> LENGTH: 25
<212> TYPE: DNA
<213> ORGANISM: Artificial sequence
<220> FEATURE:
<223> OTHER INFORMATION: Synthetic DNA

<400> SEQUENCE: 22
gagtacagcg agtactttgg cacgc                                              25

<210> SEQ ID NO 23
<211> LENGTH: 25
<212> TYPE: DNA
<213> ORGANISM: Artificial sequence
<220> FEATURE:
<223> OTHER INFORMATION: Synthetic DNA

<400> SEQUENCE: 23
tgtttcatga gggttcgcat catta                                              25

<210> SEQ ID NO 24
<211> LENGTH: 25
<212> TYPE: DNA
<213> ORGANISM: Artificial sequence
<220> FEATURE:
<223> OTHER INFORMATION: Synthetic DNA

<400> SEQUENCE: 24
taatgatgcg aaccctcatg aaaca                                              25
```